United States Patent [19]

Goldsberry

[11] Patent Number: Plant 6,641

[45] Date of Patent: Feb. 28, 1989

[54] DWARF CARNATION PLANT 'QUANDARY'

[75] Inventor: Kenneth L. Goldsberry, Fort Collins, Colo.

[73] Assignee: Colorado State University Research Foundation, Fort Collins, Colo.

[21] Appl. No.: 71,805

[22] Filed: Jul. 10, 1987

[51] Int. Cl.[4] ..... A01H 5/00

[52] U.S. Cl. ..... Plt./70

[58] Field of Search ..... Plt./70–73

*Primary Examiner*—James R. Feyrer

*Attorney, Agent, or Firm*—Edwin L. Spangler, Jr.

[57] ABSTRACT

A carnation plant known by the cultivar name Quandary was developed through a breeding program and is particularly characterized as to uniqueness by its dwarf growth habit and the following combined characteristics: upon pinching a rooted cutting, forms 4 to 6 lateral stems 24 to 26 cm long, each developing a terminal flower and 4 to 6 secondary buds which open intermittently after the terminal flowers seneses; light pink and red variegated flowers 5.0 to 6.0 cm in diameter with a slight fragrance; can be grown under specified environmental conditions either as a single pinched plant per 10 cm pot or 3 pinched plants per 13 cm pot, which results in an ideal new flowering house plant.

1 Drawing Sheet

1

My present invention relates to a new and distinct dwarf cultivar of *Dianthus caryophyllus* Linn. identified as plant 85-215-120 and given the name Quandary.

Quandary is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering houses plants.

Quandary was originated from a cross made in a controlled breeding program at the Horticulture Department, W. D. Holley Plant Environmental Research Center, Colorado State University, Fort Collins, Colo. using the unnamed seed parent 83-15-20 and an unnamed pollen parent 82-43A, also developed by the present inventor.

Quandary was discovered and selected as one flowering plant within the progeny of the stated cross by Kenneth L. Goldsberry on July 20, 1985 in a controlled environment in Fort Collins, Colo.

The first act of asexual reproduction of Quandary was accomplished when vegetative cuttings were taken, by the inventor, from the initial selection on Sept. 5, 1985 in a controlled environment in Fort Collins, Colo. The initial rooting of the cuttings and performance of the resulting plants have demonstrated that the distinctive characteristics of this new cultivar Quandary, here in disclosed, appear to be firmly fixed and hold true from generation to generation.

Quandary has not been observed under all possible environmental conditions. The phenotype may vary significantly with variation in the production environment including irrigation regimes, temperature, light intensity, day length and nutritional programs. It has been observed and evaluated, from a rooted cutting to a mature plant while being grown in Fort Collins and Denver, Colo. and Encintias and Salinas, Calif. under greenhouse conditions, which approximate those generally used in commercial practice.

2

The following traits, which have been repeatedly observed, characterize Quandary and distinguishes it as a new and distinct dwarf carnation cultivar:

1. Somatic chromosome is 2n=30
2. A double type flower, similar to commercial cut flower spray types
3. Flower sizes range from 5.0 to 6.0 cm in diameter
4. Light pink flower color with red variegation
5. Medium flowering response on a scale of early, medium or late flowering
6. Four to six lateral shoots develop following a pinch of the main stem
7. The terminal flower, four to six secondary buds, four to seven tertiary buds and three to four quaternary buds form on each flowering stem. As the old flowers senese, the secondary buds and tertiary buds continue to open and quaternary buds usually abort
8. Secondary peduncle lengths on a single stem varies between 1.8 to 7.9 cm.
9. Plant height ranges between 24.0 to 26.0 cm.
10. Little or no fragrance is present There are no dwarf carnation cultivars, for house plant use, presently developed and known to the inventor.

BRIEF DESCRIPTION OF THE DRAWING

The accompanying top colored photograph taken on May 1, 1987, using an 18 percent Kodak photographic gray card as a color base, illustrates in perspective view and the overall appearance of Quandary (85-215-120) grown in 10 cm (single plant) and 15 cm (3 plants) azalea pots. The bottom photo shows buds, inflorescence, stem, foliage characteristics and color of Quandary are typical and true as possible with illustrations of this type.

The following detailed description of my new dwarf carnation cultivar are based upon observations of greenhouse grown plants made in 1986 and 1987 at Fort Collins, Colo. The color values were determined in a standard color viewing booth with a 5000° K. fluorescent light source using references developed and published by The Royal Horticultural Society, London, England.

PLANT CHARACTERISTICS

Origin: Seedling selection.

Parentage:

*Seed parent.*—Selected unnamed seedling, 83-15-20 (Goldsberry).

*Pollen parent.*—Selected unnamed seedling 82-43A (Goldsberry).

Classification:

*Botanic.*—*Dianthus caryophyllus* Linn. cv. Quandary.

*Commercial.*—Dwarf carnation for pot plant production.

Propagation: Vegetative cuttings, 6 to 7 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Three to four lateral shoots form naturally, but are accelerated by removing the terminal portion of the main stem, at the sixth or seventh node from the top, resulting in a compact, bushy and strong up right plant. Some basal branches may elongate enough to place apical buds on a plane equal to the terminal flowers of the initial stems.

Stems: Numerous lateral branches form close to the base of the plant and vary in length from 24–26 cm, having 5 to 9 nodes with opposite leaves. A reproductive bud usually forms at each upper 4 to 6 nodes. Shoots forming at the seventh or tenth node below the terminal flower, usually develop into another flower stem in proper environmental conditions. All stems have a blue-grey glaucous condition, approximating 189B in color.

Foliage: Leaves are abundant and typical of the commercial carnation type. The longest leaves at the seventh node from the top of each stem range in length from 8.0 to 13.4 cm. The fifth node from the top has the widest leaves, 0.7 to 1.0 cm. The foliage is progressively smaller above and below these nodes. Both the upper and lower sides of the leaves are dark green and have a blue-grey glaucous condition. The color of both surfaces is identified as 189B with the surface bloom present and 137A when it is removed.

INFLORESCENCE CHARACTERISTICS

Buds: Terminal buds average 3.0 cm in length just prior to opening and the secondary buds 2.5 to 3.0 cm. The average bud circumference ranges from 5.0 cm for the terminal and 4.4 cm. for secondary buds, at the first sign of petal color. Significantly visible tertiary buds form on the peduncles of the upper six secondary buds and quaternary buds are most prevalent on tertiary buds at nodes through seven from the top of the stem. Double quaternary buds are usually present. The tertiary and quaternary buds do not open in low light conditions. All buds are oval in shape and pointed.

Sequence of development: The terminal bud on each stem will show color before any lateral bud color is visible. The opening sequence of the secondary buds is generally at node positions one, three, four, two and five from the terminal flower position on each stem. In the proper environments, new flower bearing shoots emerge from the seventh to tenth nodes below the terminal flower and at the base of the plant, creating a perpetual flowering plant in high light conditions. p0 Flowering response: A rooted cutting pinched 2 to 4 weeks after planting will flower 14 to 16 weeks following the pinch from a October 1 plant date and 11 to 12 weeks from a June 1 date in Fort Collins, Colo. when growing temperatures approximate 11° C. at night and 17° C. during the day.

Inflorescence type: Each initial stem is a semi-compound spray with a terminal bud 4 to 6 secondary, 4 to 7 tertiary, 3 to 4 quaternary buds and 3 to 5 lateral shoots.

Number of buds and flowers per stem: Each stem has a terminal flower that develops along with the upper most, of the 4 to 6 secondary buds; new flowering shoots usually form at the sixth to ninth nodes of each initial stem resulting in an average of 5.0 flowers per stem. The tertiary and quaternary buds do not develop petals in low light and many do not open.

Peduncle length: The length of the peduncles range from 1.2 cm for the top secondary bud to 7.9 cm for the lowest bud, on each stem, when the terminal flower is in prime condition. The peduncles of the tertiary buds vary from 0.7 to 3.3 cm.

Peduncle strength: Strong, holds flowers erect during all growing seasons; degree of brittleness is related to environmental conditions.

Flower:

*Size.*—Terminal flowers range in size from 5.0 to 6.0 cm and the secondaries, 5.0 to 6.0 cm depending on the environment.

*Type.*—Commercial double with 33 to 48 moderately serrated petals in the terminal flowers, which have an average length and width of 5.0 cm and 3.2 cm, respectively.

*Form.*—Sub hemispherical in longitudinal section with the petals adjacent to the calyx, slightly reflexed at maturity. Seldom splits. The secondary flowers are 4.5–6.0 cm in diameter and have average petal lengths of 4.6 cm and 2.6 cm wide. The tertiary buds may open under ideal light conditions; the quaternary buds seldom open.

Corolla color: General tonality at a distance of 1 meter: variegated with 50D as a base petal color and 53C blotches and streaks. Upper petal surface: newly opened petals are similar in color, but fade to 54CD and 49D in greenhouse conditions. Lower petal surface: have the same color characteristics as the upper surface.

Keeping quality: In the greenhouse, individual flowers remain aesthetically pleasing up to 6 days; in the home 8 to 13 days with room temperatures of 17° C. and high, natural light intensity.

Fragrance: No fragrance is specifically apparent.

Reproductive organs:

*Androecium.*—Typical carnation except has aborted 13–9 filaments, no anthers or pollen.

*Gynoecium.*—Typical of carnation in all respects; pistil is 0.7 to 1.2 cm in length and has 2 styles and stigmas. The stigmas are white at all stages of maturity.

Disease resistance: The plant has been found free of pathogen races currently associated with standard carnation cultivars, including the wilts and Etched Ring or Fleck viruses.

I claim:

1. A new and distinct cultivar of *Dianthus caryophyllus,* Linn, identified as 85-215-120 and known as Quandary and substantially as herein described and illustrated.

* * * * *

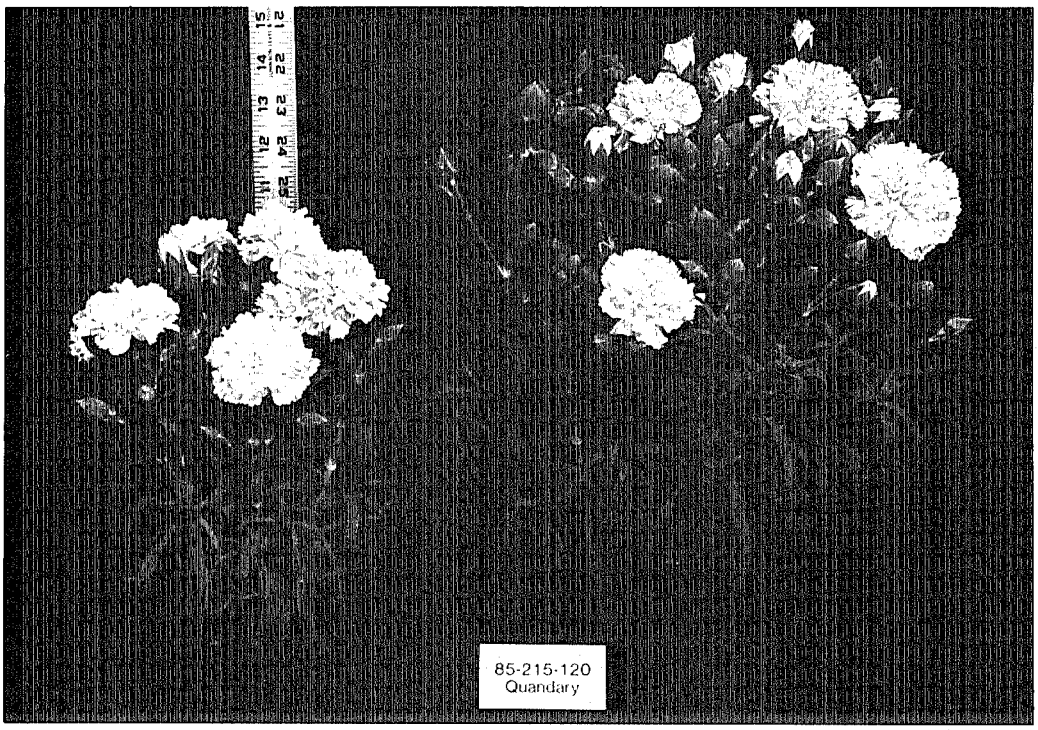
85-215-120
Quandary
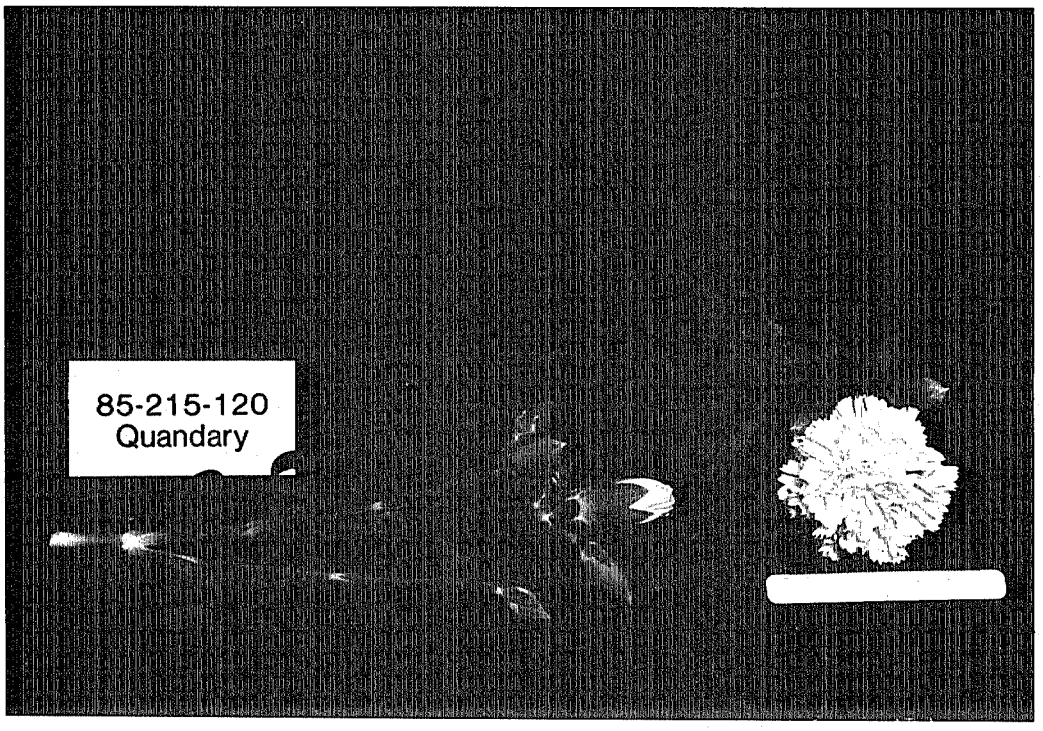
85-215-120
Quandary